(12) United States Patent
Villaseca et al.

(10) Patent No.: US 7,013,180 B2
(45) Date of Patent: Mar. 14, 2006

(54) CONDITIONING OF COUPLED ELECTROMAGNETIC SIGNALS ON A LEAD

(75) Inventors: Eduardo H. Villaseca, deceased, late of Minneapolis, MN (US); by Bonnie A Dougherty, legal representative, Minneapolis, MN (US); Garry L. Dublin, Maple Grove, MN (US); Gregory J. Haubrich, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 610 days.

(21) Appl. No.: 10/136,798

(22) Filed: Apr. 30, 2002

(65) Prior Publication Data

US 2003/0144721 A1 Jul. 31, 2003

Related U.S. Application Data

(63) Continuation-in-part of application No. 10/059,598, filed on Jan. 29, 2002, now abandoned.

(51) Int. Cl.
*A61N 1/05* (2006.01)

(52) U.S. Cl. .................. 607/116; 607/119; 607/122; 607/63; 600/373; 600/374; 128/901

(58) Field of Classification Search .................. 607/115, 607/116, 119, 122, 2, 9, 63, 123; 600/411, 600/372, 373, 374, 377; 128/901, 902, 908
See application file for complete search history.

(56) References Cited

U.S. PATENT DOCUMENTS

| | | | | |
|---|---|---|---|---|
| 3,871,382 | A | * | 3/1975 | Mann .......................... 607/37 |
| 3,968,802 | A | * | 7/1976 | Ballis ............................ 607/9 |
| 5,217,010 | A | | 6/1993 | Tsitlik et al. .......... 128/419 PG |
| 5,246,438 | A | * | 9/1993 | Langberg ..................... 606/33 |
| 5,398,683 | A | | 3/1995 | Edwards et al. |
| 5,629,622 | A | | 5/1997 | Scampini ..................... 324/247 |
| 5,697,958 | A | | 12/1997 | Paul et al. .................... 607/31 |
| 5,722,998 | A | | 3/1998 | Prutchi et al. ................ 607/30 |
| 5,964,705 | A | | 10/1999 | Truwit et al. |
| 6,101,417 | A | | 8/2000 | Vogel et al. ................... 607/30 |

FOREIGN PATENT DOCUMENTS

| | | |
|---|---|---|
| WO | WO 92/21278 | 12/1992 |
| WO | WO 99/60370 | 11/1999 |
| WO | WO 00/48512 | 8/2000 |

\* cited by examiner

*Primary Examiner*—Kennedy Schaetzle
(74) *Attorney, Agent, or Firm*—Girma Wolde-Michael (57) ABSTRACT

A method and an apparatus for reducing coupled electrical energy resulting from an electromagnetic field. Embodiments of the present invention provide for an elongate body having a proximal end portion, a middle portion, and a distal end portion and at least one coil wound about at least one of the proximal end portion, the middle portion, and the distal end portion, the coil to provide for filtering of radio frequency (RF) signal-coupled electrical energy.

8 Claims, 9 Drawing Sheets

CONDITIONING OF COUPLED ELECTROMAGNETIC SIGNALS ON A LEAD

This application is a continuation-in-part of application Ser. No. 10/059,598, filed Jan. 29, 2002 now abandoned.

BACKGROUND OF THE INVENTION

1. Field of the Invention

This invention relates generally to implantable medical devices, and, more particularly, to a method and apparatus for trapping and/or conditioning electromagnetic phenomenon resulting from electromagnetic fields experienced by a medical device lead.

2. Description of the Related Art

The technology explosion in the implantable medical devices industry has resulted in many new and innovative devices and methods for analyzing and improving the health of a patient. The class of implantable medical devices now includes pacemakers, cardioverters, defibrillators, neural stimulators, and drug administering devices, among others. Today's state-of-the-art implantable medical devices are vastly more sophisticated and complex than early ones, capable of performing significantly more complex tasks. The therapeutic benefits of such devices have been well proven.

There are many implementations of implantable medical devices that provide data acquisition of important physiological data from a human body. Many implantable medical devices are used for cardiac monitoring and therapy. Often these devices comprise sensors that are placed in blood vessels and/or chambers of the heart. Often these devices are operatively coupled with implantable monitors and therapy delivery devices. For example, such cardiac systems include implantable heart monitors and therapy delivery devices, such as pace makers, cardioverter, defibrillators, heart pumps, cardiomyostimulators, ischemia treatment devices, drug delivery devices, and other heart therapy devices. Most of these cardiac systems include electrodes for sensing and gain amplifiers for recording and/or driving sense event signals from the inter-cardiac or remote electrogram (EGM).

Generally, a number of physiological data such as ventricular pressure, oxygen supply in the patient's blood, EGM data, a patient's breathing patterns, and the like, are collected and stored by data acquisition devices implanted into a human body. The data can then be used to analyze the condition of a patient's physical state. Many times, information gathered by the implantable medical device may provide indications of certain conditions in a patient's body. Such conditions may affect the manner in which medical therapy (e.g., cardiac therapy) is delivered by the implantable medical device. If a particular condition is not detected properly, or a condition is misdiagnosed, incorrect reactions by the implantable medical device may occur. Incorrect reactions by the implantable medical device may cause harm to a patient. Generally, physiological data may be collected by a lead that delivers a signal relating to the physiological data to implantable medical device. In the presence of an electromagnetic field, the signal on the lead may become corrupted, causing errors.

Many times, delivery of therapy may be performed in response to certain physiological data and/or data indicating other physical occurrences (e.g., unusual breathing patterns) detected in a patient. For example, certain activities performed by a patient may lead to increased physiological indications in the patient's body. Often, an implantable medical device may be programmed to detect such physiological changes and react to them accordingly. For example, an implantable medical device may deliver one or more cardiac therapy in response to a particular condition detected in the patient's body. The implantable medical device may also modify the normal mode of therapy delivery in a patient's body in response to an unusual condition detected. Therefore, improved accuracy in the signal delivered by the lead is desirable for proper operation of the implantable medical device.

When an implantable medical device has been inserted into a patient's body, it enters an area where the patient is exposed to a substantial amount of radio frequency (RF) signals. The length of the lead generally acts as an antenna during exposure to radio frequency signals, such as magnetic resonance imaging (MRI) processes and RF signals from radio diathermy processes. Due to the antenna-like behavior of the lead, the tip of the lead may behave as a source for the coupled (e.g., induced) current flow created by the RF signal. Furthermore, other portions of the lead, such as part that is placed inside a connector associated with the implantable medical device, may experience coupled (e.g., induced) current flow created by the RF signal.

In the presence of MRI signals, (e.g., during MRI scanning processes), an appreciable amount of current may be generated in the lead such that the tip of the lead contains a sizable magnitude of current gradient. Due to the conservation of energy principles, much of the current is converted to heat due to the energy loss caused by the resistance of the lead tip. Therefore, a significant amount of heat may be generated at the tip of the lead, which may cause serious bodily injury to a patient. Burns to the tissue exposed to the tip of the lead may occur. Furthermore, a large amount of coupled current in the lead may cause the implantable medical device to malfunction, thereby creating a risk of injury or death to the patient.

Changes to the signals traveling though the lead (e.g., sensor signals from the lead to the implantable medical device and/or therapy signals sent by the device) may cause the malfunctions in the operation of the implantable medical device. In such an instance, erroneous delivery of therapy may occur which may lead to heart arrhythmia or other physiological damage to a patient.

The present invention is directed to overcoming, or at least reducing the effects of, one or more of the problems set forth above.

SUMMARY OF THE INVENTION

In one aspect of the present invention, an apparatus is provided for reducing coupled current resulting from an electromagnetic field in a medical electrical lead. The medical electrical lead comprises an elongate body having a proximal end portion, a middle portion, and a distal end portion and at least one coil wound about at least one of the proximal end portion, the middle portion, and the distal end portion, the coil to provide for filtering of radio frequency (RF) signal-coupled currents.

In another aspect of the present invention, a system is provided for reducing coupled current resulting from an electromagnetic field in a medical electrical lead. The system of the present invention comprises an implantable medical device and a medical electrical lead operatively coupled to the implantable medical device. The medical electrical lead comprises a proximal end portion, a middle portion, and a distal end portion and at least one coil wound about at least one of the proximal end portion, the middle portion, and the distal end portion. The coil provides an inductive impedance in parallel with a capacitive impedance for reducing coupled currents resulting in the presence of an electromagnetic field.

In yet another aspect of the present invention, a method is provided for reducing coupled current resulting from an electromagnetic field in a medical electrical lead. The method comprising providing at least one wound coil around at least one of a proximate end portion, a middle portion, and a distal end portion of the medical electrical lead such that the coil provides an inductive impedance in parallel with a capacitive impedance to reduce the coupled current.

BRIEF DESCRIPTION OF THE DRAWINGS

The inventions may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are many discrete processes involving the operation of implantable medical devices (e.g., pacemakers, cardio defibrillators, and the like). The operation of an implantable medical device includes collecting, storing, and analyzing physiological data relating to a patient, and/or delivering therapy (e.g., cardiac therapy) to a portion of a patient's body. Often, these tasks are performed by an implantable medical system, which includes an implantable medical device. Based upon the analysis performed by the implantable medical system, one or more therapies may be delivered to a particular portion of a patient's body. One example of such a therapy is a cardiac therapy, which is delivered to a patient's heart. Interpretation of the physiological data and/ or data relating to unusual activities in the patient's body is important in determining the behavior (e.g., therapy deliver patterns, etc.) of the implantable medical device.

Embodiments of the present invention provide for reducing the coupled (e.g., induced) current in a lead caused by RF signals present around the lead. Embodiments of the present invention provide for inserting a coil proximate to the tip of the lead to substantially isolate the tip from the lead, thereby reducing the possibility of inducement of an undesirable amount of current coupled or induced by RF signals, on the lead. Embodiments of the present invention provide for attaching a coil proximate to the tip of a lead, wherein an inductor in series with the resistivity of the lead is effectively created. Embodiments of the present invention provide for a circuit whose effective resonance occurs at radio frequency signals such that an open circuit is created for radio frequency coupled current signals present on the lead. In other words, the coil provided by embodiments of the present invention provide an open circuit or high impedance for high frequency signals, at the same time providing a normal signal path for low frequency signals such as pacing signals or data acquisition signals.

Figure 1:
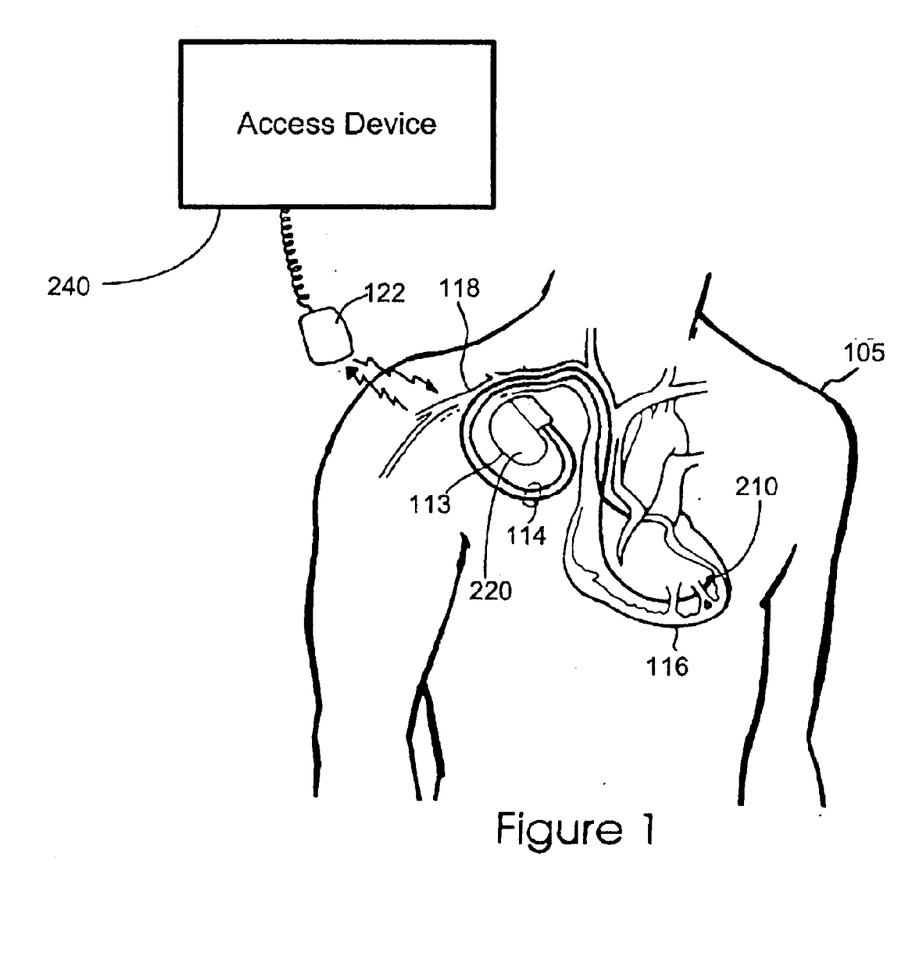
FIG. 1 is a simplified diagram of an implementation of an implantable medical device, in accordance with one illustrative embodiment of the present invention.

Turning now to FIG. 1, one embodiment of implementing an implantable medical device into a human body is illustrated. A sensor/therapy delivery device 210 (e.g., devices attached to leads 114) placed upon the heart 116 of the human body 105 is used to acquire and process physiological data. An implantable medical device 220 collects and processes a plurality of data acquired from the human body 105. In one embodiment, the implantable medical device 220 may be a pacemaker or a defibrillator. The data acquired by the implantable medical device 220 can be monitored by an external system, such as the access device 240 comprising a programming head 122, which remotely communicates with the implantable medical device 220. The programming head 122 is utilized in accordance with medical device programming systems known to those skilled in the art having the benefit of the present disclosure, for facilitating two-way communication between the pacemaker 220 and the access device 240.

In one embodiment, a plurality of access devices 240 can be employed to collect a plurality of data processed by the implantable medical device 220 in accordance with embodiments of the present invention. The pacemaker 220 is housed within a hermetically sealed, biologically inert outer canister or housing 113, which may itself be conductive so as to serve as an electrode in the pacemaker 220 pacing/ sensing circuit. One or more pacemaker sensors/leads, collectively identified with reference numeral 114 in FIG. 1, are electrically coupled to the pacemaker 220 and extend into the patient's heart 116 via a vein 118. Disposed generally near a distal end of the leads 114 are one or more exposed conductive electrodes (sensor/therapy delivery unit 210) for receiving electrical cardiac signals or delivering electrical pacing stimuli to the heart 116. The leads 114 may be implanted with their distal end situated in either the atrium or ventricle of the heart 116. In an alternative embodiment, the sensors 210, or the leads 114 associated with the sensors 210, may be situated in a blood vessel on the heart 116 via a vein 118.

Figure 2:
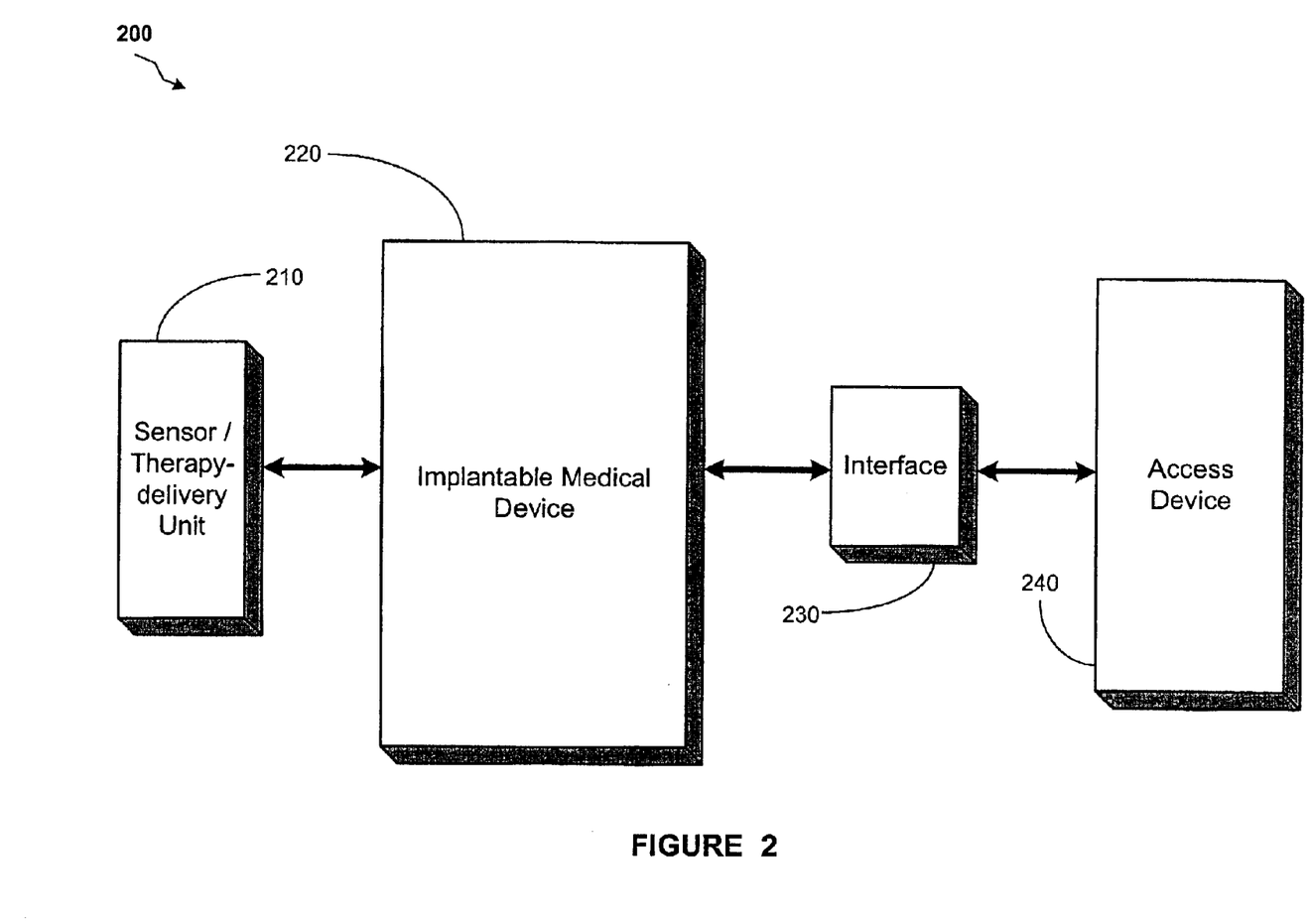
FIG. 2 illustrates a simplified block diagram representation of an implantable medical system in accordance with one illustrative embodiment of the present invention.

Turning now to FIG. 2, a system 200, in accordance with one embodiment of the present invention, is illustrated. The system 200 comprises a sensor/therapy delivery unit 210, an implantable medical device 220, and an access device 240. Embodiments of the present invention provide a plurality of physiological data and non-physiological data from the sensor/therapy delivery unit 210 to the implantable medical device 220, which are then processed and stored in the implantable medical device 220. The sensor/therapy delivery unit 210 may comprise a plurality of sensors that are capable of acquiring physiological and non-physiological data. Based upon data from the sensor(s) 210 and other factors, the implantable medical device 220 may deliver a therapy to a portion of the patient's body 105, via the sensor/therapy delivery unit 210. The access device 240, which may communicate to the device 220 via an interface 230 (e.g., an interface internal to the device 220), can be used reprogram and/or make modifications to the operation of the implantable medical device 220. In one embodiment, a lead 114 (described below) coupled to the implantable medical device 220 is used to house the sensor(s) 210 and/or the therapy delivery electrodes.

Figure 3:
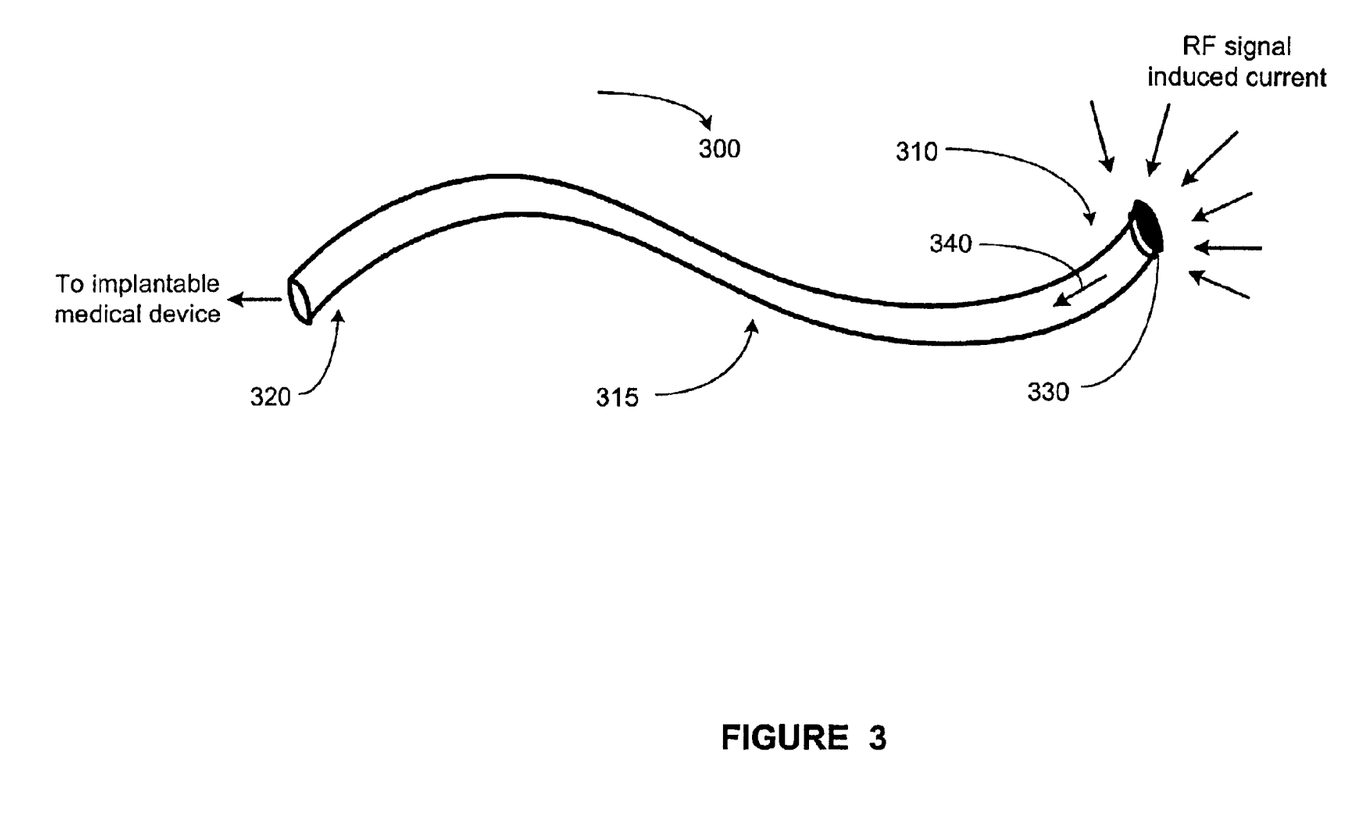
FIG. 3 illustrates a stylized depiction of a lead used in the implantable medical system, in accordance with one embodiment of the present invention.

Turning now to FIG. 3, a medical electrical lead 300, which may be coupled to the implantable medical device 220, is illustrated. The lead 300 may be connected to an implantable medical device 220 at approximately a proximal end portion 320 of the lead 300. The lead 300 also comprises a middle portion 315, and a distal end portion 310 at the end of which is a tip 330. As illustrated in FIG. 3, radio frequency (RF) signal coupled current present around the lead 300 may cause a current flow 340 in the lead 300. At the tip 330, a RF signal source is effectively created due to the RF signals present around the lead 300.

In the presence of significant electromagnetic fields, such as fields present during an MRI processes, a substantial amount of RF signal-coupled energy (e.g., a current and/or a voltage) may be present around the tip 330 of the lead 300. Therefore, the large amount of current 340 may be present at the tip 330, which causes an energy transfer due to the resistivity of the lead 300. Generally, the energy transfer due to the resistivity of the lead tip 330 to tissue interface is transferred in the form of heat. This causes the tip 330 of the lead 300 to become heated. The heat from the tip 330 of the lead 300 may then be transferred to the tissues surrounding the tip 330, causing harm to the patient's body. The electrical energy 340 generally occurs at the high RF frequencies, such as the MRI frequencies of 64 MHz and/or 128 MHz, or such as a radio diathermy frequency 27 MHz. If the electrical energy 340 were effectively blocked, the heat generated at the tip 330 would be substantially reduced.

Figure 4:
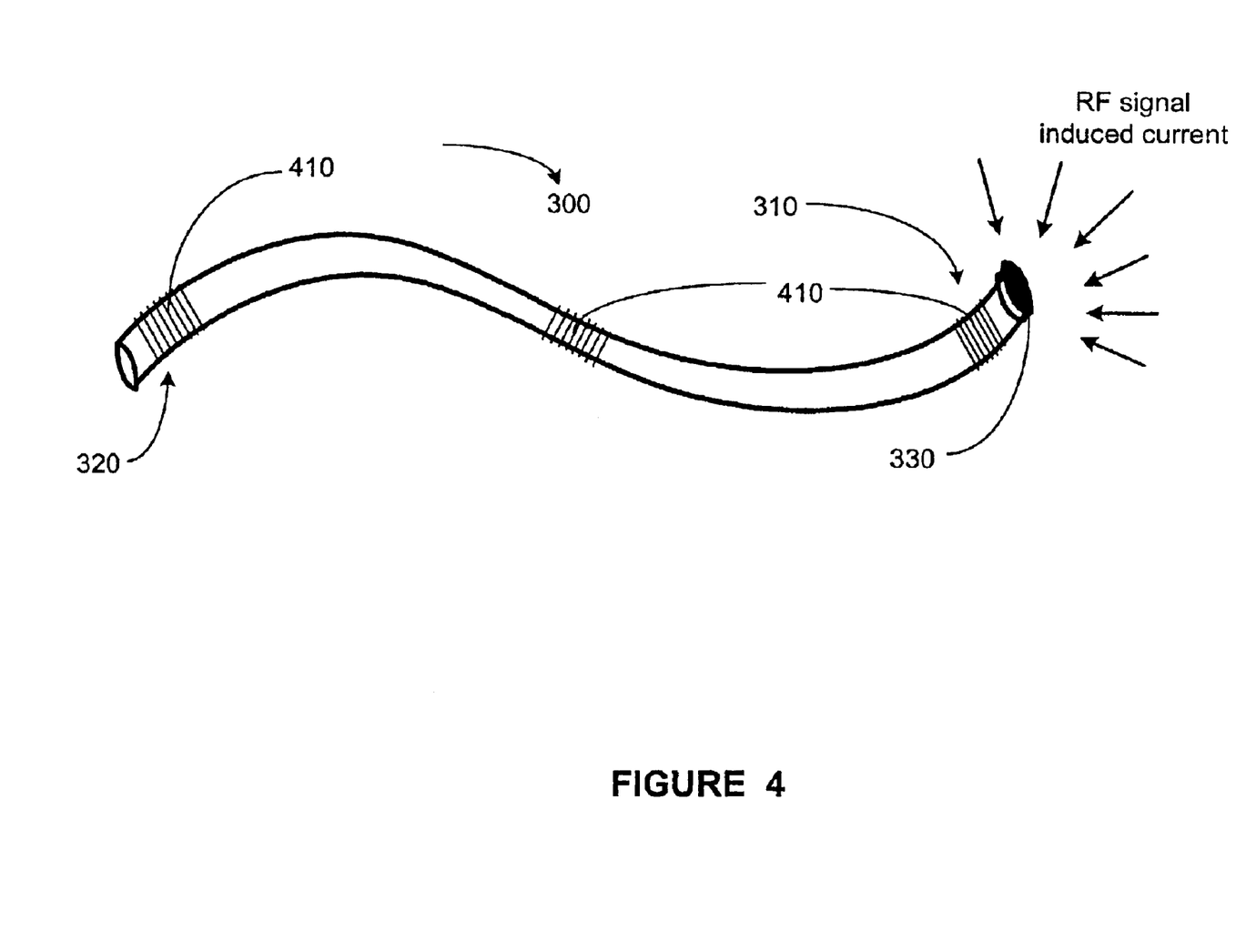
FIG. 4 illustrates a stylized depiction of the distal end of the lead used in the implantable medical system, in accordance with one embodiment of the present invention.

Turning now to FIG. 4, a coil 410 is attached to the lead 300 near the tip 330 of the lead 300. In one embodiment, a plurality of coils 410 may be placed at other portions of the lead 300, such as at the proximate end portion 320 and/or at the middle section/portion 315 of the lead 300. Placing the coil 410 at the distal end 310 of the lead 300 may prevent appreciable amounts of high frequency electrical energy 340 from traveling through the extent of the length of the lead 300. Effectively, the coil 410 acts as an electromagnetic filter and/or trap, which are capable of trapping/filtering RF signal-electrical energy 340, such as electrical energy coupled by the presence of an MRI signal. Inductive and capacitive effects due to the implementation of the coil 410 (described in greater detail below) reduce the flow of high-frequency currents 340 through the tip 330 of the lead 300. Therefore, heat generated due to the high-frequency current's 340 interaction with the resistivity of the lead tip 330 is reduced as a result of the implementation of the coil 410. Similarly, coils 410 placed at other portions of the lead also provide the benefit of reducing high-frequency currents 340 in the lead tip 330.

Figure 5:
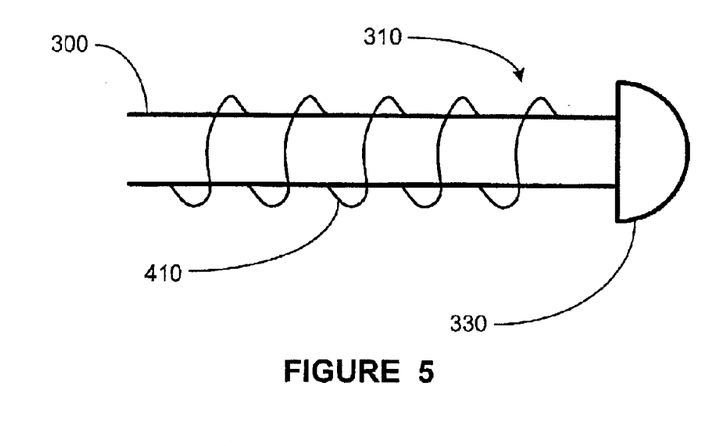
FIG. 5 illustrates a stylized depiction of a coil implemented on the lead used in the implantable medical system, in accordance with one embodiment of the present invention.

Turning now to FIG. 5, an enlarged view of the distal end 310 of the lead 300 and the coil 410, is illustrated. The coil 410 is wrapped around the lead 300 near the tip 330. The coil 410 provides the function of an inductor, whose inductive properties at higher signal frequencies, such as 64 and/or 128 MHz. As an example, the outer diameter of the spool of the coil 410 may be approximately 50 to 60 thousandths of an inch. The length of the coil 410 may be approximately one tenth to three tenths of an inch. It should be appreciated that other measurements may be implemented to achieve the results taught by embodiments of the present invention. The amount of windings of the coil 410 can be varied to affect the capacitive and inductive effects created by the coil 410. Therefore, the windings of the coil 410 can be adjusted to provide capacitive and inductive properties for a variety of frequencies of currents resulting from electromagnetic fields. These capacitive and inductive properties may form a parallel inductor-capacitor circuit network that may be resonant.

Figure 6A:
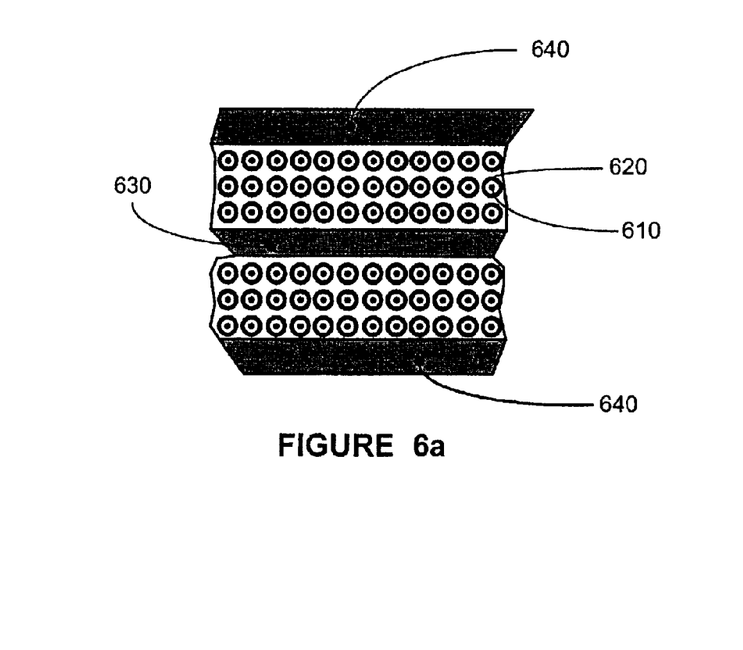
FIG. 6 illustrates stylized depiction of a cross-sectional view of the coil implemented on the lead used in the implantable medical system, in accordance with one embodiment of the present invention.
Figure 6B:
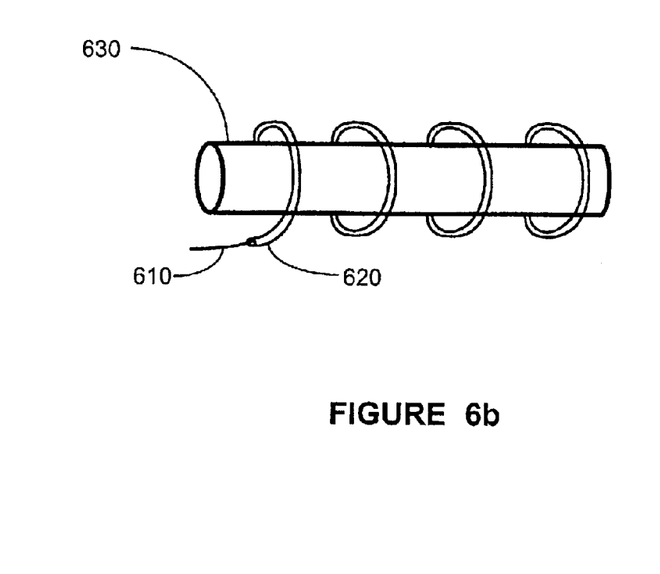

In one embodiment, the coil 410 is made up of a wire that is insulated. Turning now to FIGS. 6a and 6b, a cross sectional view of a portion of the coil 410 and a 3-dimensional view of a portion of the coil 410, respectively, are illustrated. In one embodiment, the wire within the coil 410 comprises conductive materials such as copper, gold, silver, MP35N, platinum, and the like. It should be appreciated that a variety of conductive materials 610 may be used in accordance with embodiments of the present invention. Furthermore, an insulated coating 640 that insulates the wire 610 is a dielectric material, such as an enamel coating. The wire is wound about a dielectric (non-conductive) core 630 and encapsulated by a dielectric outer shell 640. The wire itself may have an insulating coating as well. Due to the insulation of the coil 410, the portion of the lead 300 covered by the coil 410 is not electrically conducted to its surrounding, therefore, it does not function as an anode or an electrical return path of current into the body of the patient. However, the conductive material 610 of the coil 410 provides for electrical characteristics within the electrical path of the lead 300. In other words, the conductive material 610 of the coil 410 adds capacitive and/or inductive characteristics to the electrical path of the lead 300 in a series fashion.

Figure 7A:
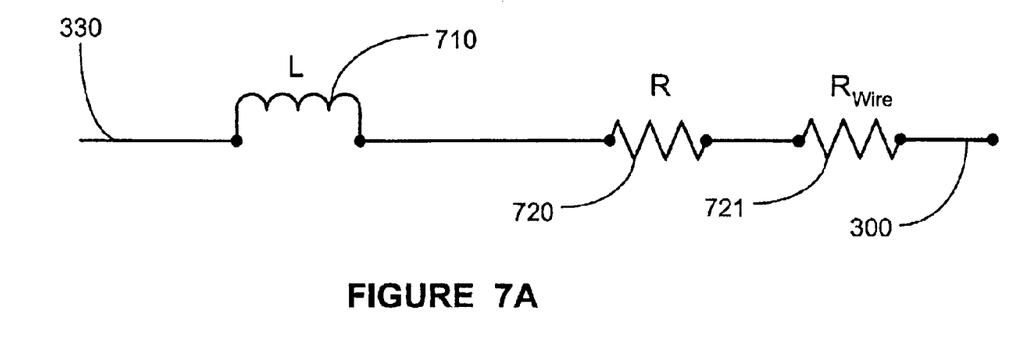
FIGS. 7a–7i illustrate equivalent electrical circuit-diagram representations of the various implementations of coil(s) placed on the lead used in the implantable medical system, in accordance with at least one embodiment of the present invention.

Turning now to FIGS. 7A–7I, equivalent electrical circuits that result from various implementations of the coil 410 onto the lead 300, are illustrated. In one embodiment, the coil 410 provides an equivalent inductance in series with the electrical flow path of the lead 300, as illustrated in FIG. 7A. The coil 410 provides an inductor L 710 in series with an equivalent resistance R 720 (which in one embodiment is the equivalent resistance of the coil 410) in the electrical path of the lead 300, which terminates at the ring tip 330. Furthermore, the circuit in FIG. 7A also comprises an equivalent resistance ($R_{wire}$ 721) of the lead-wire itself. The inductor L 710 becomes effective during the presence of an RF signal, such as an MRI signal of 64 MHz and/or 128 MHz. It should be appreciated the frequency at which the inductor L 710 becomes effective may be modified by changing the winding of the coil 410 and remain within the spirit of embodiments of the present invention.

At low frequencies, such as a signal delivering a pacing signal to the tip 330 of the lead 300, the inductance L 710 is an equivalent electrical-short within the lead 300. As RF signal frequency signals surround the lead 300, the inductor L 710 provides an inductance of various measurements, depending on the windings and/or the size of the conductive material 610 of the wire associated with the coil 410. In one embodiment, the inductor L 710 is approximately 4.7 micro Henries, which is effectively active during the presence of an MRI signal field. This electrical effect is also present in the presence of radio frequency signals. The 4.7 micro Henry inductor may reduce the instantaneous build-up of high-frequency currents coupled by significant electromagnetic fields, such as fields caused by an MRI process, but not limited to MRI processes.

The coil 410 is wound and designed such that the inductor L 710 created by the coil 410 may be resonant with radio frequency signals such as 64 MHz and 128 MHz signals. In an alternative embodiment, the coil 410 may provide a substantially large inductance without resonance. Therefore, at RF signal frequencies a large amount of impedance is present in the lead 300, thereby providing a large obstacle for RF coupled currents in the lead 300. Effectively, a high impedance circuit is created at the location of the inductor L 710 (for high-frequency electrical energy) during the presence of high frequency signal. The high impedance near the tip 330 of the lead 300 provided by the coil 410 at high frequencies, causes most of the length of the lead 300 to be ineffective for inducement of signals caused by RF signals. At the same time, the coil 410 allows the passage of low frequency signals utilized by the implantable medical device 220. The inductive reactance provided by the inductor L 710 significantly isolates high frequency (radio frequency) coupled signals in the lead 300 from the lead tip 330.

Figure 7B:
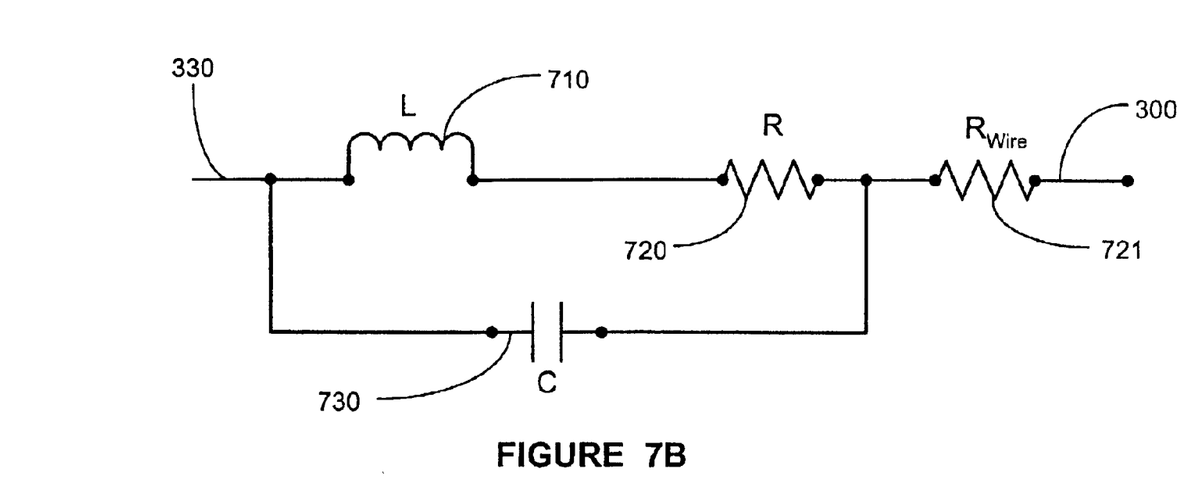

Turning now to FIG. 7B, an alternative embodiment of the equivalent circuit provided by the coil 410 at the tip 330 of the lead 300 is illustrated. The coil 410 may be wound in such a manner around the lead 300 that a capacitance C 730 is also created. The capacitance C 730 exists in parallel across the inductor L 710. The capacitance C 730 is in parallel with the inductor L 710 and the resistance R 720, which are in series with equivalent of the coil 410 and $R_{wire}$ 721. The capacitance C 730 is generally due to the parasitic capacitance that is formed across each of the windings of the coil 410. Generally, the capacitance C 730 is effective during the presence of high-frequency signals at the tip 330 of the lead 300. The capacitance C 730 generally does not interfere with low-frequency signals on the lead 300, such as pacing signals sent by the implantable medical device 220 and/or physiological sensor signals traveling to the device 220.

The capacitance C 730 represents an equivalent capacitance of a combination of the plurality of parasitic capacitance across the windings of the coil 410. The combination of the parallel configuration of the inductor L 710 and the capacitor C 730 provides a parallel circuit that is of a higher impedance than the inductor L 710 by itself. Therefore, the circuit provided by the coil 410 provides for a broader range of frequencies in which significant high impedance at high frequencies is created near the tip 330 of the lead 300.

In one embodiment, the inductor L 710 and the capacitor C 730 provides a self-resonant circuitry that reacts various RF signals, particularly to 27 MHz, 64 MHz, and/or to 128 MHz signals. The resonance causes a high impedance at the RF signals, such that electrical energy coupled by the RF signals are significantly isolated. The isolation of the high frequency electrical energy provides the benefit of reducing of heating at the tip 330 of the lead 300. By changing the diameter of the conductive material (wire) 610 in the coil 410 and/or changing the number of windings of the coil 410, the self-resonant circuitry can be designed to react at a variety of predetermined range of high frequency signals. This principle can be used to adapt embodiments of the present invention to respond to changing frequency implementation of MRI processes.

Figure 7C:
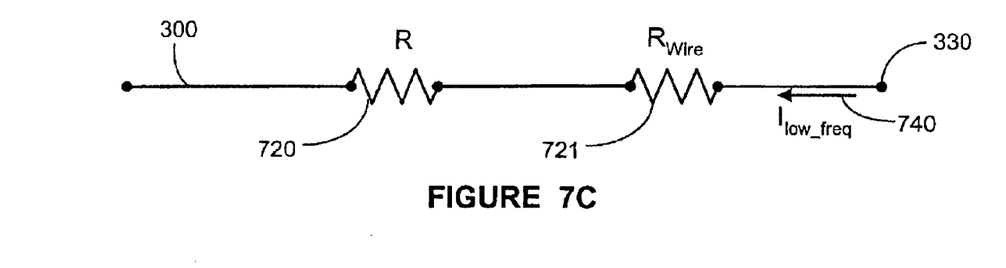

As shown in FIG. 7C, at low frequencies, the low-frequency current ($l_{low\_freq}$) 740 flows through the lead 300 through the resistor $R_{wire}$ 721 to the resistor R 720 (e.g., approximately 3 Ohms in one embodiment), which is the equivalent resistance of the lead-wire and of the coil, respectively. In one embodiment, the equivalent resistance of the lead-wire $R_{wire}$ 721 may be a small resistor of small value, such as a 35 Ohms resistor. Therefore, low-frequency signals, such as pacing signals and/or therapy delivery signals, can flow through the lead 300 and through the tip 330 to the tissue surrounding the tip 330. In other words, the coil 410 does not interfere with normal operation of therapy delivery and/or physiological data collection performed by the implantable medical device 220. However, at high frequencies, the inductor L 710 and/or the capacitance C 730 provide high impedance (see FIGS. 7C and 7D).

Figure 7D:
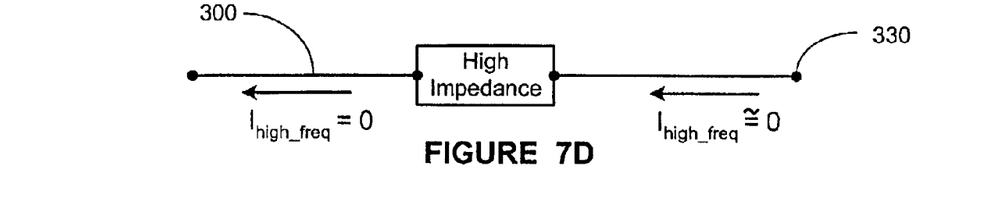

At high frequencies, the electrical energy coupled by RF signals that is present at the lead tip 330 is approximately zero due to the resonance nature of the impedance provided by the inductor L 710 and the capacitance C 730.

Figure 7E:
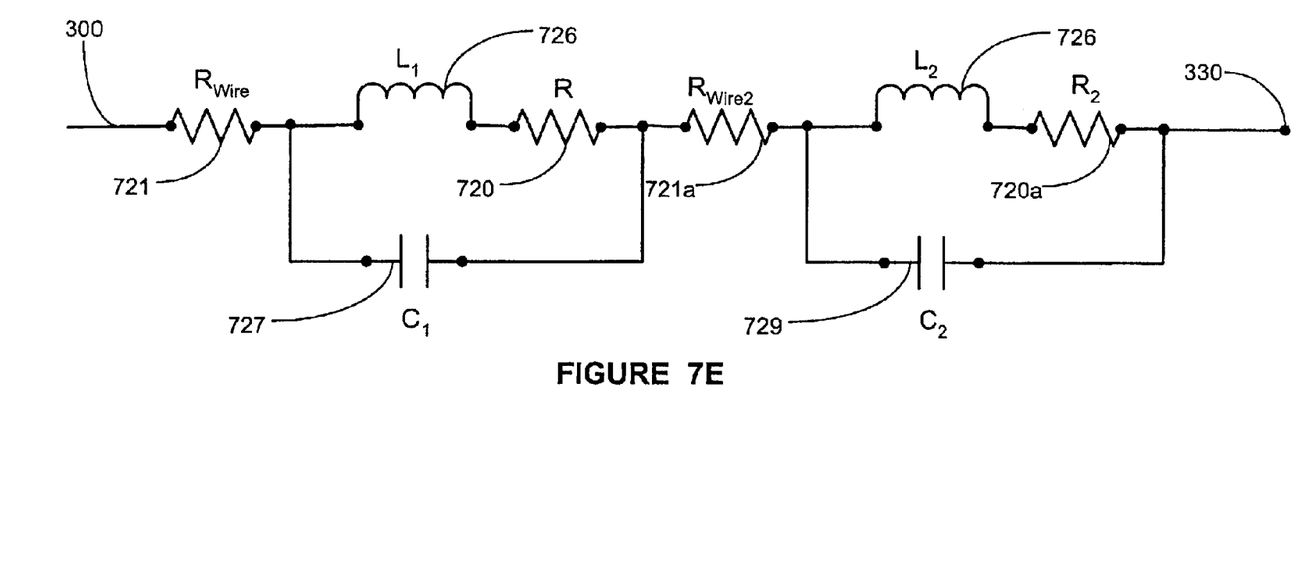

At high frequencies, a high impedance is present as a result of the coil 410, substantially reducing the value of the electrical energy coupled by RF signals ($l_{high\_freq}$) at the lead tip 330. Implementation of one or more coils may produce a multi-stage circuit illustrated in FIG. 7E. FIG. 7E illustrates two parallel sets of inductors and capacitors. The parallel combination of inductor $L_1$ 726 (in series with R 720), both in parallel with capacitor $C_1$ 727 is in series (through a second wire resistance value $R_{wire2}$ 721a) with the parallel combination of inductor $L_2$ 728 (in series with a second equivalent resistance value $R_2$ 720a), both in parallel with capacitor $C_2$ 729, providing the high impedance effect at high frequencies illustrated in FIG. 7D. The capacitors $C_1$ 727 and $C_2$ 729 may comprise lumped element(s) or parasitic capacitance. In one embodiment, each set of parallel capacitor/inductor sets of FIG. 7E may respond to a different frequency signals, thereby providing the high impedance benefits of FIG. 7D at a plurality of frequencies.

Figure 7F:
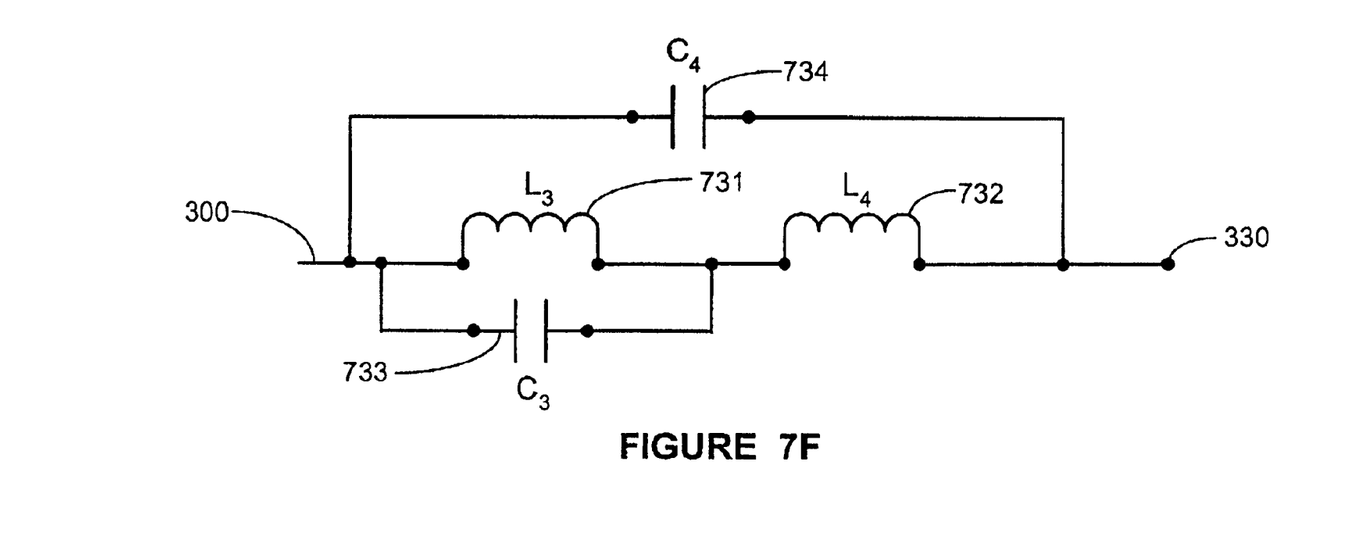

Implementation of the coils 410 as described by embodiments of the present invention may be configured to produce an equivalent circuit illustrated in FIG. 7F. FIG. 7F illustrates a parallel combination of capacitor $C_3$ 733 and inductor $L_3$ 731 in series with inductor $L_4$ 732, all in parallel with capacitor $C_4$ 734, providing a multi-frequency response to provide a high-impedance obstacle for coupled high-frequency electrical energy. In one embodiment, inductor $L_3$ 731 may be a tapped inductor and capacitors $C_3$ 733 and $C_4$ 734 may be comprised of lumped elements.

Figure 7G:
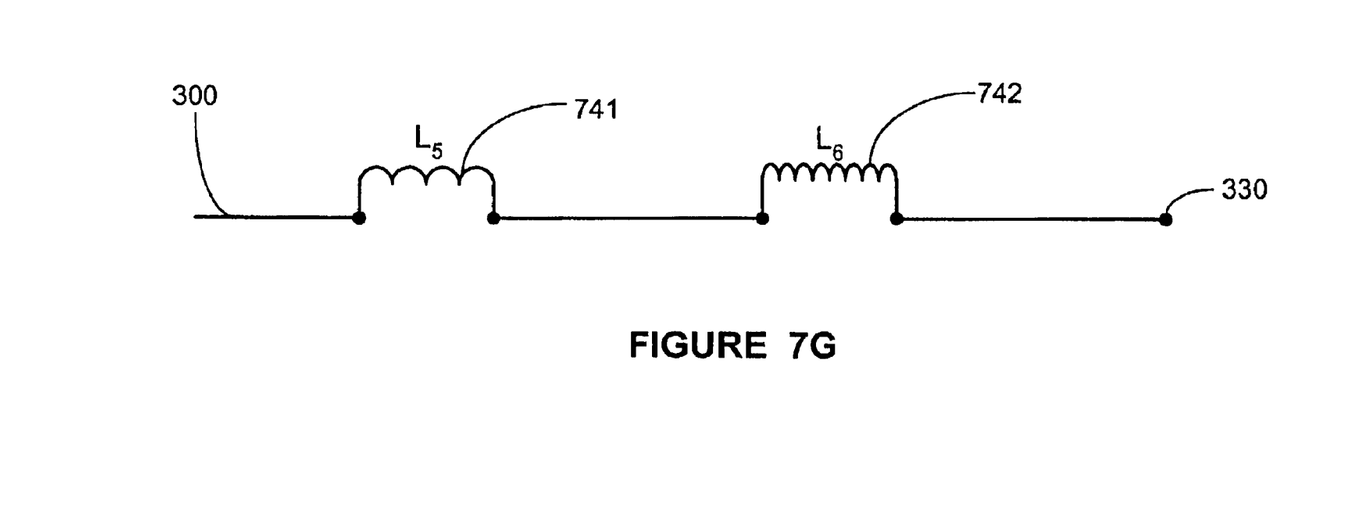

A plurality of coils 410 may be implemented on the lead 300 to provide protection against coupled high-frequency electrical energy caused by a plurality of signals of different frequencies. For example two coils 410, one wound more loosely that the other, may be implemented on a lead 300. This would produce an equivalent circuit that comprises two different inductors, as illustrated in FIG. 7G. FIG. 7G provides an inductor $L_5$ 741 that is of a different value with a series inductor $L_6$ 742, which results from a coil 410 that is more tightly wound than the coil 410 that produces the inductor $L_5$ 741. Therefore, the respective inductors $L_5$ 741 and $L_6$ 742 can provide high-impedance obstacles to different coupled electrical energy resulting from two different signals of varying frequencies. The equivalent parasitic capacitance associated with each coil 410 is also different.

Figure 7H:
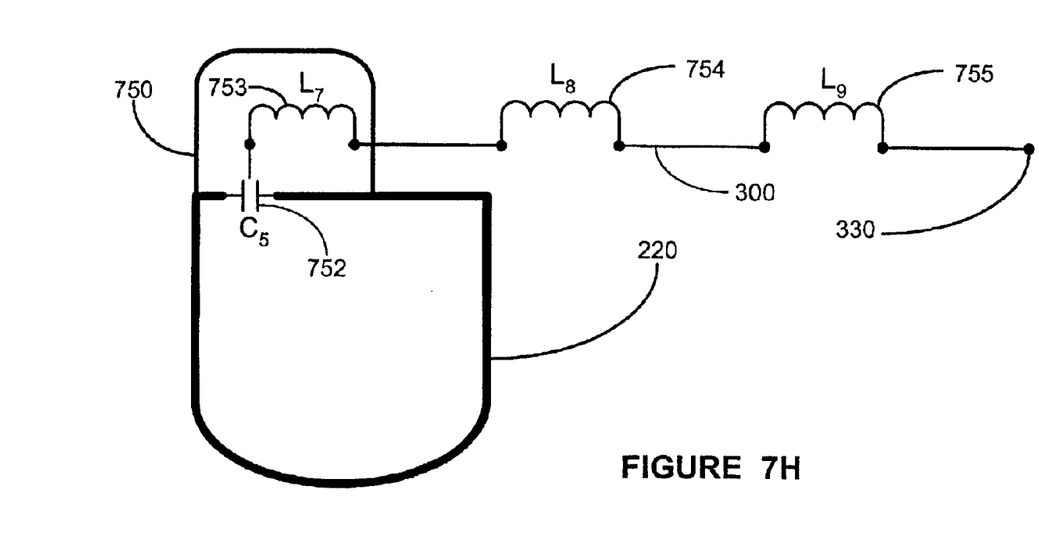

FIG. 7H illustrates implementation of coils 410 on lead 300 connected to an implantable medical device. The lead 300 is connected to a connector module/block 750, which is integrated with the implantable medical device 220. The connector block 750 comprises a capacitor $C_5$ 752, which in one embodiment is a feed-through capacitor. In one embodiment, three coils 410 are implemented on the lead 300 to produce three inductors, $L_7$ 753, $L_8$ 754, and $L_9$ 755. The inductor $L_7$ 753 is within the connector block 750, and interacts with $C_5$ 752 to produce a low pass filter, which substantially blocks high-frequency signals and allows the flow of low-frequency signals to the device 220. The inductor $L_8$ 754 acts as filter to break-up the resonant length of the lead 300. The inductor $L_9$ 755 provides protection against the induction of high-frequency electrical energy at the tip of the lead 300, as described above.

Figure 7I:
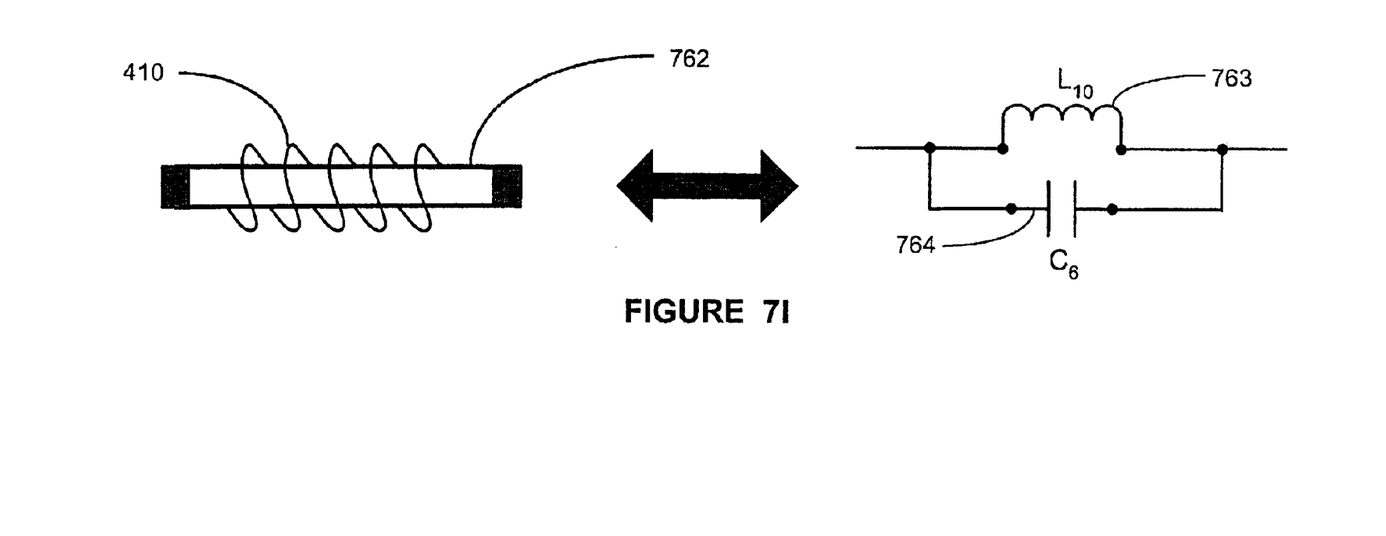

The concept of implementing the coil 410, as described in embodiments of the present invention, may be extended by winding a coil on a capacitor, as illustrated in FIG. 7I. As illustrated in FIG. 7I, a coil 410 is wound around a capacitor 762, which may be implemented on a lead 300. This provides the ability to generate an equivalent circuit that more precisely responds to particular high-frequency signals. The coil 410 wound around the capacitor 762 produces an parallel combination of a capacitor $C_6$ 764 and an inductor $L_{10}$ 763, which can be used to provide a high impedance obstacle to coupled high frequency electrical energy with increased accuracy. The capacitor $C_6$ 764 and an inductor $L_{10}$ 763 may be implemented onto a variety of portions of the lead 300, including the proximate end 320, the middle portion 315, and/or the distal end 310 of the lead 300.

The equivalent circuits provided by FIGS. 7A–7I significantly reduce the high frequency electrical energy in the lead tip 330 due to exposure to radio frequency signals, such as MRI signals, diathermy signals, and a variety of other high-frequency signals, or output. The embodiments illustrated by FIGS. 7A–7I may be used individually or in any combination to produce high-impedance response called for by embodiments of the present invention.

The above detailed description is an illustrative example of an embodiment in accordance with the present invention, of the implementation of the implantable medical device 220 described above. It should be appreciated that other implementations and/or embodiments can be employed within the spirit of the present invention. The teachings of the present invention can be utilized for a variety of systems relating to electrical circuitry, including circuitry that utilize stored charge.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is set forth in the claims below.

What is claimed:

1. A medical electrical lead, comprising:
    an elongate body including a proximal end portion, a middle portion and a distal end portion; and
    a first coil wound about at least one of said proximal end portion, said middle portion, and said distal end portion, and a second coil wound about at least one of said proximal end portion, said middle portion, and said distal end portion, said first coil being wound more loosely than said second coil such that said second coil provides at least one of a different inductance compared to an inductance provided by said first coil, and a different parallel parasitic capacitance compared to a parasitic capacitance provided by said first coil;
    wherein the coils provide filtering of radio frequency (RF) signal-coupled electrical energy at at least one of said proximal end portion and said distal end portion.

2. A medical electrical lead, comprising:
    a pacing tip;
    an connector end adapted for connecting with an implantable device connector block;
    an electrical flow path extending between the connector end and the pacing tip; and
    a plurality of inductive coils, each in series with the electrical flow path;
    wherein at least one of the plurality of inductive coils is adapted to filter RF signal-coupled electrical energy traveling along the flow path toward the pacing tip.

3. The lead of claim 2, wherein another of the plurality of inductive coils is adapted to filter RF signal-coupled electrical energy traveling toward the connector end.

4. The lead of claim 2, wherein the plurality of inductive coils includes a first coil and a second coil, the first coil having an inductance greater than that of the second coil.

5. The lead of claim 2, further comprising a capacitor in parallel with a one of the plurality of inductive coils.

6. The lead of claim 5, wherein the one of the plurality of inductive coils is wound about the capacitor.

7. The lead of claim 2, further comprising a plurality of capacitors, each in parallel with a one of the plurality of inductive coils.

8. The lead of claim 2, wherein a one of the plurality of inductive coils is positioned in a middle portion of the electrical flow path, between the connector end and the pacing tip, acting as a filter of RF signal-coupled electrical energy in order to break up a resonant length of the electrical flow path.

* * * * *